(12) United States Patent
DaSilva et al.

(10) Patent No.: US 6,435,582 B1
(45) Date of Patent: Aug. 20, 2002

(54) OBJECT MANIPULATOR AND MANIPULATION SYSTEM

(75) Inventors: Antonio Manuel DaSilva, Irvine; Eric Cotera Brooks, Long Beach, both of CA (US)

(73) Assignee: Motoman, Inc., West Carrollton, OH (US)

( * ) Notice: Subject to any disclaimer, the term of this patent is extended or adjusted under 35 U.S.C. 154(b) by 3 days.

(21) Appl. No.: 09/628,969

(22) Filed: Jul. 31, 2000

(51) Int. Cl.$^7$ ................................................ B66C 1/42
(52) U.S. Cl. ........................................ 294/94; 294/87.1
(58) Field of Search ........................... 294/87.1, 94, 95, 294/116, 115; 414/618, 744.8; 901/39

(56) References Cited

U.S. PATENT DOCUMENTS

| | | | |
|---|---|---|---|
| 2,524,880 A | * | 10/1950 | Cattonar et al. |
| 3,012,811 A | * | 12/1961 | Sandrock |
| 3,652,117 A | * | 3/1972 | Schroeder |
| 4,262,795 A | * | 4/1981 | Hecker |
| 4,379,581 A | * | 4/1983 | Perry |
| 4,492,512 A | * | 1/1985 | Mink |
| 4,694,951 A | * | 9/1987 | Gibbemeyer |
| 4,930,976 A | * | 6/1990 | Spacher et al. |
| 4,974,458 A | | 12/1990 | Koike |
| 5,102,287 A | * | 4/1992 | Johnson et al. |
| 5,255,574 A | | 10/1993 | Wuerschum |
| 5,260,872 A | | 11/1993 | Copeland et al. |
| 5,306,510 A | | 4/1994 | Meltzer |
| 5,397,542 A | | 3/1995 | Nelms et al. |
| 5,536,056 A | | 7/1996 | Clarke et al. |
| 5,589,137 A | | 12/1996 | Markin et al. |
| 5,735,387 A | | 4/1998 | Polaniec et al. |
| 5,775,755 A | | 7/1998 | Covert et al. |
| 5,814,276 A | | 9/1998 | Riggs |

FOREIGN PATENT DOCUMENTS

| | | |
|---|---|---|
| EP | 0 251 441 B1 | 12/1993 |
| EP | 0 240 733 B1 | 12/1994 |

* cited by examiner

*Primary Examiner*—Victor Batson
(74) *Attorney, Agent, or Firm*—Killworth, Gottman, Hagan & Schaeff LLP

(57) ABSTRACT

An object manipulation system is provided including a plurality of objects arranged in an object plane, an X-Y positioner, and an object manipulator. The X-Y positioner is arranged to move within an X-Y plane displaced from and parallel to the object plane. The object manipulator is coupled to the X-Y positioner so as to be movable with the X-Y positioner. The object manipulator comprises a rotary turret assembly and a plurality of gripper assemblies. The rotary turret assembly defines a plurality of gripper assembly stations and a gripper pick/place position. The rotary turret assembly is arranged to rotate the gripper assembly stations about a turret axis so as to position a selected one of the gripper assembly stations in the pick/place position. The gripper assemblies are arranged in respective ones of the gripper assembly stations. The rotary turret assembly includes a gripper actuator assembly arranged to cause a gripper assembly positioned in the pick/place position to execute an object pick/place operation on one of the objects in the object plane.

36 Claims, 10 Drawing Sheets

OBJECT MANIPULATOR AND MANIPULATION SYSTEM

BACKGROUND AND SUMMARY OF THE INVENTION

The present invention relates to the manipulation of selected objects and, more particularly, to a robotic system in which objects are selectively picked from one location and placed in another location. The present invention is particularly well-suited for picking and placing objects held in a closely spaced array of similar objects. Test tubes, for example, are often stored or temporarily held in a tray including an array of closely spaced test tubes of like size. The object manipulator of the present invention may be utilized in an object manipulation system to move selected test tubes to and from the array of closely spaced tubes.

In accordance with one embodiment of the present invention, an object manipulator is provided including a gripper assembly arranged to grip and release an object. The gripper assembly comprises a plurality of gripper fingers, a gripper finger pivot assembly, and a finger spreader. Each of the gripper fingers includes a camming surface portion, a bearing surface portion, and an object engaging portion. The gripper finger pivot assembly is arranged to accommodate respective bearing surface portions of the plurality of gripper fingers. The finger spreader is positioned to progressively engage respective camming surface portions of the plurality of gripper fingers. The gripper fingers are shaped and the pivot assembly is arranged such that progressive engagement of respective camming surface portions by the finger spreader causes the object engaging portions to be drawn away from each other and such that progressive disengagement of respective camming surface portions and the finger spreader causes the object engaging portions to be drawn towards each other.

The camming surface portion, the bearing surface portion, and the object engaging portion may be arranged in succession along each of the gripper fingers. The object engaging portion may include a layer of object gripping material formed thereon. The bearing surface portion may be substantially straight.

The gripper finger pivot assembly may be arranged to define respective passages there through, and wherein the respective passages are arranged to accommodate respective bearing surface portions of the plurality of gripper fingers. The bearing surface portions of the plurality of gripper fingers may define a circular finger cross section and the respective passages may define a circular passage cross section slightly larger than the circular finger cross section. The respective passages may be defined by separate mating portions of the gripper finger pivot assembly;

A biasing member may be arranged to urge the object engaging portions towards each other. The biasing member may comprise a constrictive band arranged about the gripper fingers. The biasing member may be arranged to oppose progressive engagement of respective camming surface portions by the finger spreader.

The plurality of gripper fingers may be shaped such that, upon progressive engagement of the camming surface portions by the finger spreader, a path of movement of the object engaging portions follows a path of movement of the camming surface portions.

The finger spreader may be arranged to initially engage the camming surface portions at a first cross sectional portion thereof and subsequently engage the camming surface at progressively larger cross sectional portions thereof. The first cross sectional portion and the progressively larger cross sectional portions of the finger spreader may be circular.

An axial stop may be provided against which the camming surface portions are arranged to rest upon disengagement of the camming surface portions and the finger spreader. The axial stop may define an axial stop cross section that is no larger than a cross section of an object to be manipulated. The axial stop may define a circular axial stop cross section. The finger spreader may be arranged to progressively engage and disengage the camming surface portions by moving along the axial stop.

A gripper finger bracket may be arranged along the gripper fingers between respective camming surface portions and respective bearing surface portions. The gripper finger bracket may be arranged to define respective finger bracket apertures through which respective gripper fingers move upon progressive engagement and disengagement of the camming surface portions by the finger spreader. The respective finger bracket apertures may define an arcuate shape.

In accordance with another embodiment of the present invention, an object manipulator is provided comprising a rotary turret assembly and a plurality of gripper assemblies. The rotary turret assembly defines a plurality of gripper assembly stations and a gripper pick/place position. The rotary turret assembly is arranged to rotate the gripper assembly stations about a turret axis so as to position a selected one of the gripper assembly stations in the pick/place position. The plurality of gripper assemblies are arranged in respective ones of the gripper assembly stations. The rotary turret assembly includes a gripper actuator assembly arranged to cause a gripper assembly positioned in the pick/place position to execute an object pick/place operation.

The plurality of gripper assemblies may be removably secured in respective ones of the gripper assembly stations. The gripper actuator may be arranged to remove a gripper assembly positioned in the pick/place position from one of the gripper assembly stations. The plurality of gripper assemblies may be removably secured in respective ones of the gripper assembly stations through magnetic coupling of the gripper assemblies and the gripper assembly stations.

Each of the gripper assemblies may comprise a plurality of gripper fingers and a finger spreader positioned to progressively engage respective camming surface portions of the plurality of gripper fingers. The gripper assembly may be arranged such that progressive engagement of respective camming surface portions of the gripper fingers by the finger spreader causes object engaging portions of the gripper fingers to be drawn away from each other and such that progressive disengagement of respective camming surface portions of the gripper fingers and the finger spreader causes the object engaging portions to be drawn towards each other. The gripper actuator may be further arranged to actuate a finger spreader of a gripper assembly positioned in the pick/place position following removal of the gripper assembly from one of the gripper assembly stations. The gripper actuator assembly may further comprise a spreader actuator arranged to engage a selected finger spreader and move the selected finger spreader along an axis parallel to the turret axis. The gripper actuator assembly may further comprise a Z-axis drive arranged to move a selected gripper assembly along a Z-axis parallel to the turret axis.

The object manipulator may further comprise a bar code reader secured to the object manipulator and defining a field of view encompassing the pick/place position.

In accordance with yet another embodiment of the present invention, an object manipulation system is provided comprising a plurality of objects arranged in an object plane, an X-Y positioner, and an object manipulator. The X-Y positioner is arranged to move within an X-Y plane displaced from and parallel to the object plane. The object manipulator is coupled to the X-Y positioner so as to be movable with the X-Y positioner. The object manipulator comprises a rotary turret assembly and a plurality of gripper assemblies. The rotary turret assembly defines a plurality of gripper assembly stations and a gripper pick/place position. The rotary turret assembly is arranged to rotate the gripper assembly stations about a turret axis so as to position a selected one of the gripper assembly stations in the pick/place position. The gripper assemblies are arranged in respective ones of the gripper assembly stations. The rotary turret assembly includes a gripper actuator assembly arranged to cause a gripper assembly positioned in the pick/place position to execute an object pick/place operation on one of the objects in the object plane.

Additional X-Y positioners may be arranged to move parallel to the object plane in the same work cell as the original positioner. In which case, additional object manipulators may be coupled to each of the additional X-Y positioners.

Accordingly, it is an object of the present invention to provide scheme whereby objects may be selectively picked from one location and placed in another location. Other objects of the present invention will be apparent in light of the description of the invention embodied herein.

BRIEF DESCRIPTION OF THE SEVERAL VIEWS OF THE DRAWINGS

The following detailed description of the preferred embodiments of the present invention can be best understood when read in conjunction with the following drawings, where like structure is indicated with like reference numerals and in which.

DETAILED DESCRIPTION

Figure 1B:
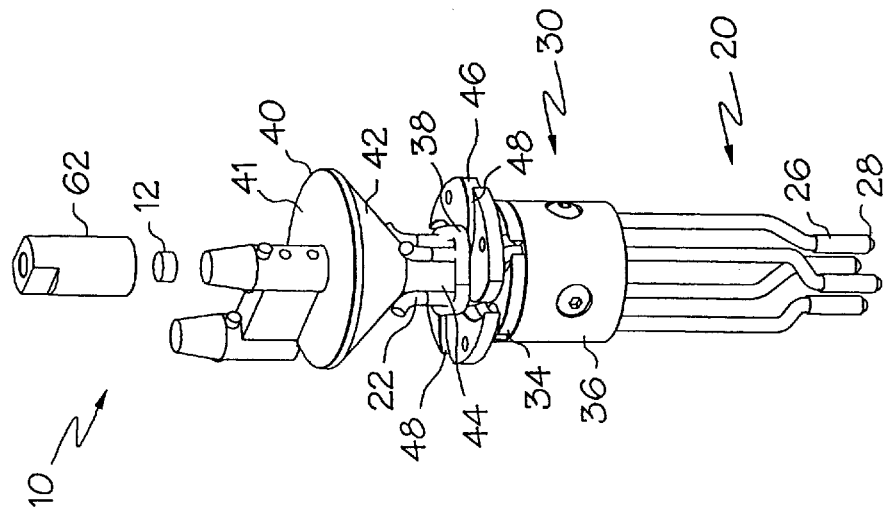
FIGS. 1A and 1B illustrate a closed gripper assembly according to the present invention.
Figure 1A:
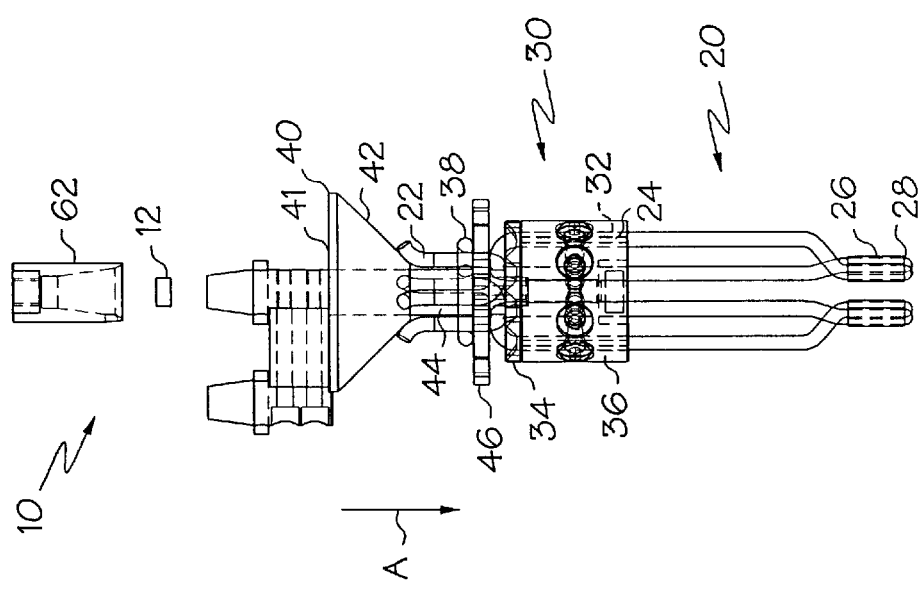

Referring initially to FIGS. 1A and 1B, a gripper assembly 10 according to the present invention is illustrated. The gripper assembly 10 is arranged to grip and release an object. In the embodiment illustrated in FIGS. 3–7, the object 100 comprises a test tube. However, it should be noted that the present invention may be utilized to manipulate objects other than test tubes as well.

The gripper assembly 10 comprises a set of gripper fingers 20, a gripper finger pivot assembly 30, and a finger spreader 40. Each of the gripper fingers 20 include a camming surface portion 22, a substantially straight bearing surface portion 24, and an object engaging portion 26 arranged in succession along each of the gripper fingers 20.

The object engaging portions 26 include a layer 28 of rubber or other object gripping material. Four gripper fingers 20 are illustrated in the figures of the present invention; however, it is noted that as few as two gripper fingers 20 may be provided. The gripper fingers also include a radial portion 25 designed to help define a path of movement of the fingers 20 upon engagement and to prevent the gripper fingers 20 from simply moving directly downwards when engaged by the finger spreader 40. It is contemplated by the present invention that the gripper fingers 20 need not be identical and that the illustrated design, shape, and profile of each gripper finger 20 may be modified to suit the demands of specific applications of the present invention.

The gripper finger pivot assembly 30 is arranged to accommodate respective bearing surface portions 24 of the plurality of gripper fingers 20. Specifically, the gripper finger pivot assembly 30 is arranged to define respective passages 32 there through which accommodate the respective bearing surface portions 24. The respective passages 32 are defined by separate mating portions 34, 36 of the gripper finger pivot assembly 30. The bearing surface portions 24 define a circular finger cross section and the respective passages 32 define a circular passage cross section slightly larger than the circular finger cross section. In this manner, each gripper finger 20 is pivotally secured by the gripper finger pivot assembly 30.

A spring, constrictive band, or other type of biasing member 38 is arranged about the gripper fingers 20 so as to urge the object engaging portions 26 towards each other, i.e., towards the closed position of FIGS. 1A and 1B, and oppose progressive engagement of respective camming surface portions 22 by the finger spreader 40. As is illustrated in FIGS. 1A, 1B, 2A and 2B, the plurality of gripper fingers 20 are shaped such that, upon progressive engagement of the camming surface portions 22 by the finger spreader 40, a path of movement of the object engaging portions 26 follows a path of movement of the camming surface portions 22. The finger spreader 40 is arranged to initially engage the camming surface portions 22 at a first cross sectional portion of the spreader and subsequently engage the camming surface 26 at progressively larger cross sectional portions of the finger spreader 40. In the illustrated The finger spreader 40 is positioned to progressively engage respective coming surface portions 22 of the plurality of gripper fingers 20. The figures clearly show an inclined outer surface 42 of the finger spreader on which the camming surface portions engage. For the purposes of describing and defining the present invention, progressive engagement or disengagement should be taken to describe a condition where successive portions of the finger spreader 40 engage or disengage the respective camming surface portions 22 of the gripper fingers 20. For example, in the illustrated embodiment, successive points along the inclined surface 42 of the finger spreader may be presented for engagement with the camming surface portions 22.

The gripper fingers 20 are shaped and the pivot assembly 30 is arranged such that progressive engagement of respective camming surface portions 22 by the finger spreader 40 causes the object engaging portions 26 to be drawn away from each other and such that progressive disengagement of respective camming surface portions 22 and the finger spreader 40 causes the object engaging portions 26 to be drawn towards each other. Stated differently, the gripper fingers 20 open as the finger spreader 40 moves in the direction A and the gripper fingers 20 close as the finger spreader 40 moves in the direction B. FIGS. 1A and 1B illustrate the gripper fingers 20 in the closed position. FIGS.

2A and 2B illustrate the gripper fingers 20 in the open position. As clearly shown in FIGS. 1A, 1B, 2A, and 2B, the each gripper finger pivots about an axis that is parallel to the longitudinal axis of that particular gripper finger. embodiment, the first cross sectional portion and the progressively larger cross sectional portions of the finger spreader 40 are circular.

The camming surface portions 22 are arranged to rest against an axial stop 44 upon disengagement of the camming surface portions 22 and the finger spreader 40. In the illustrated embodiment, the finger spreader 40 is arranged to progressively engage and disengage the camming surface portions 22 by moving along the axial stop 44 in the opposite directions A, B. Preferably, the axial stop 44 defines an axial stop cross section that is no larger than a cross section of an object to be manipulated. In the example where the object to be manipulated comprises a test tube or other object with a substantially circular cross section, the axial stop 44 may define a circular axial stop cross section with a diameter that substantially matches, or is slightly smaller than the cross section of the object to be manipulated.

Figure 2B:
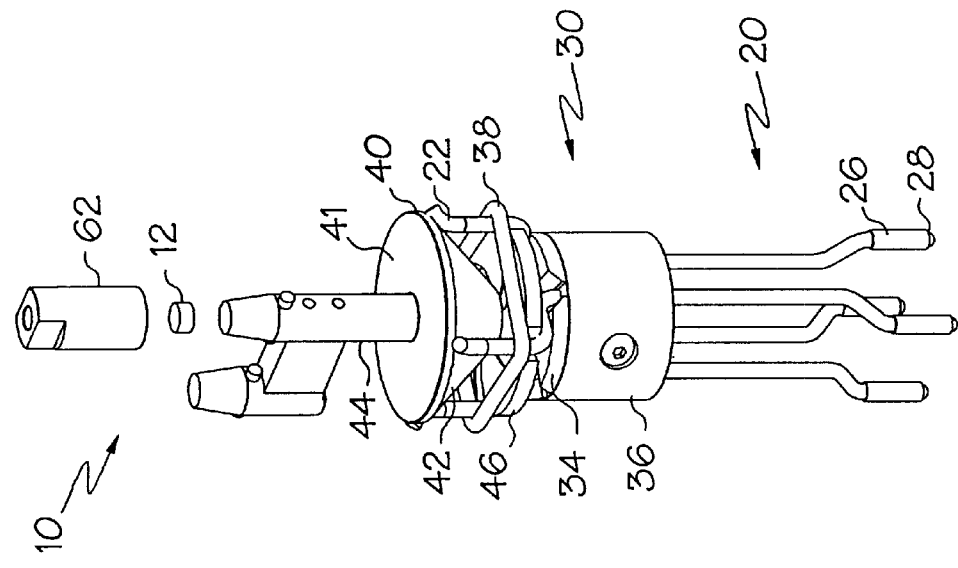
FIGS. 2A and 2B illustrate an open gripper assembly according to the present invention.
Figure 2A:
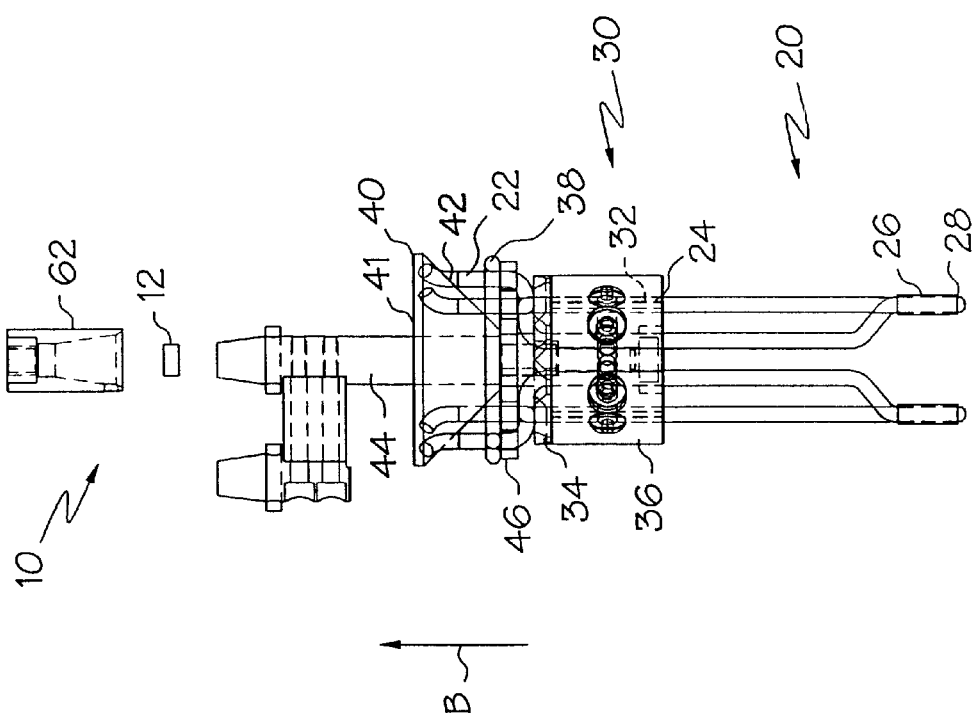

A gripper finger bracket 46 is arranged along the gripper fingers 20 between respective camming surface portions 22 and respective bearing surface portions 24. The gripper finger bracket 46 is arranged to define respective arcuate finger bracket apertures 48 through which respective gripper fingers 20 move upon progressive engagement and disengagement of the camming surface portions by the finger spreader 40. A comparison of FIGS. 1B and 2B illustrates the path of movement of the gripper fingers 20 through the respective finger bracket apertures 48. The bracket 46 serves to keep the biasing member 38 from slipping down the gripper fingers (see FIG. 2B).

Figure 6:
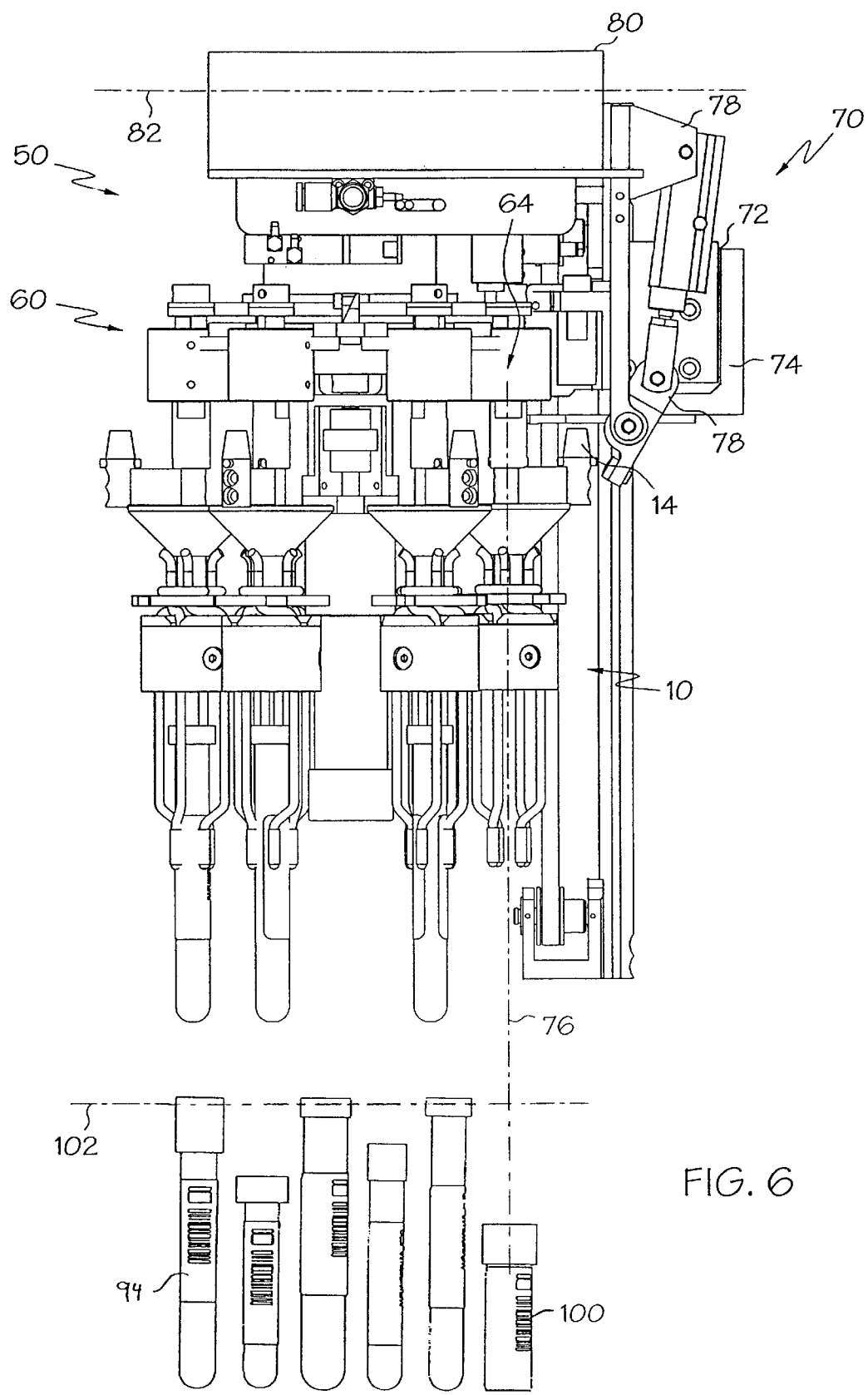
FIGS. 6–9 illustrate an object pick/place operation according to the present invention.

As is illustrated in FIG. 6, the gripper assembly 10 of the present invention is particularly well-suited for manipulating objects of a variety of different shapes and sizes. More specifically, the gripper assembly 10 of the present invention is able to grasp objects of differing shapes and sizes because the individual fingers 20 of the gripper assembly are effectively spring loaded and movable along independent paths and axes. In addition, the gripper assembly 10 is well suited for picking and placing closely spaced objects including oversized caps or top portions because the object engaging portions 26 of the gripper fingers 20 are small in diameter and converge radially inwards relative to the bearing surface portions 24 of the gripper fingers 20. In one application of the present invention, the gripper assembly 10 is utilized for picking and placing test tubes spaced 22 mm on center.

Figure 3:
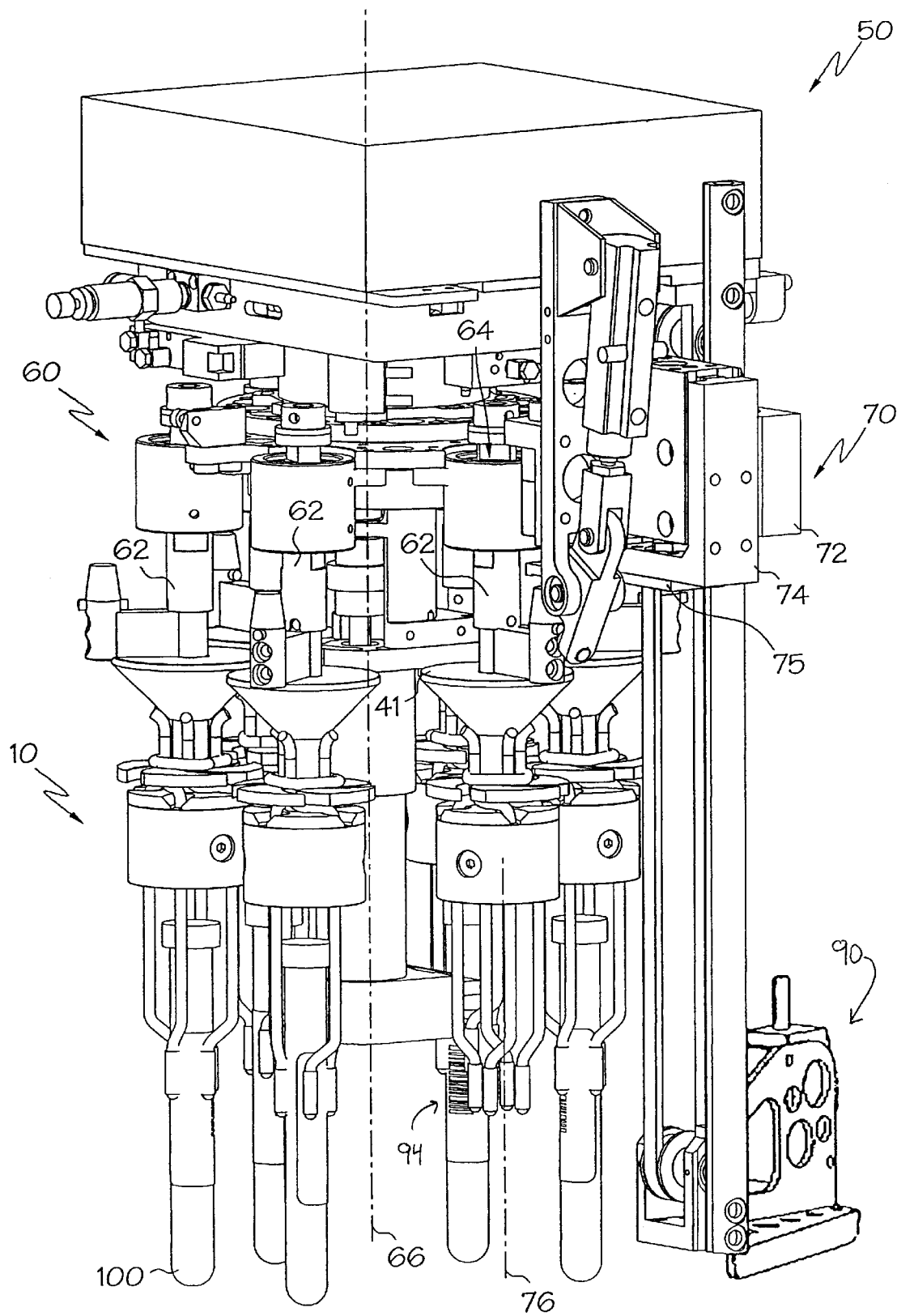
FIGS. 3 and 4 are isometric illustrations of an object manipulator according to the present invention.
Figure 4:
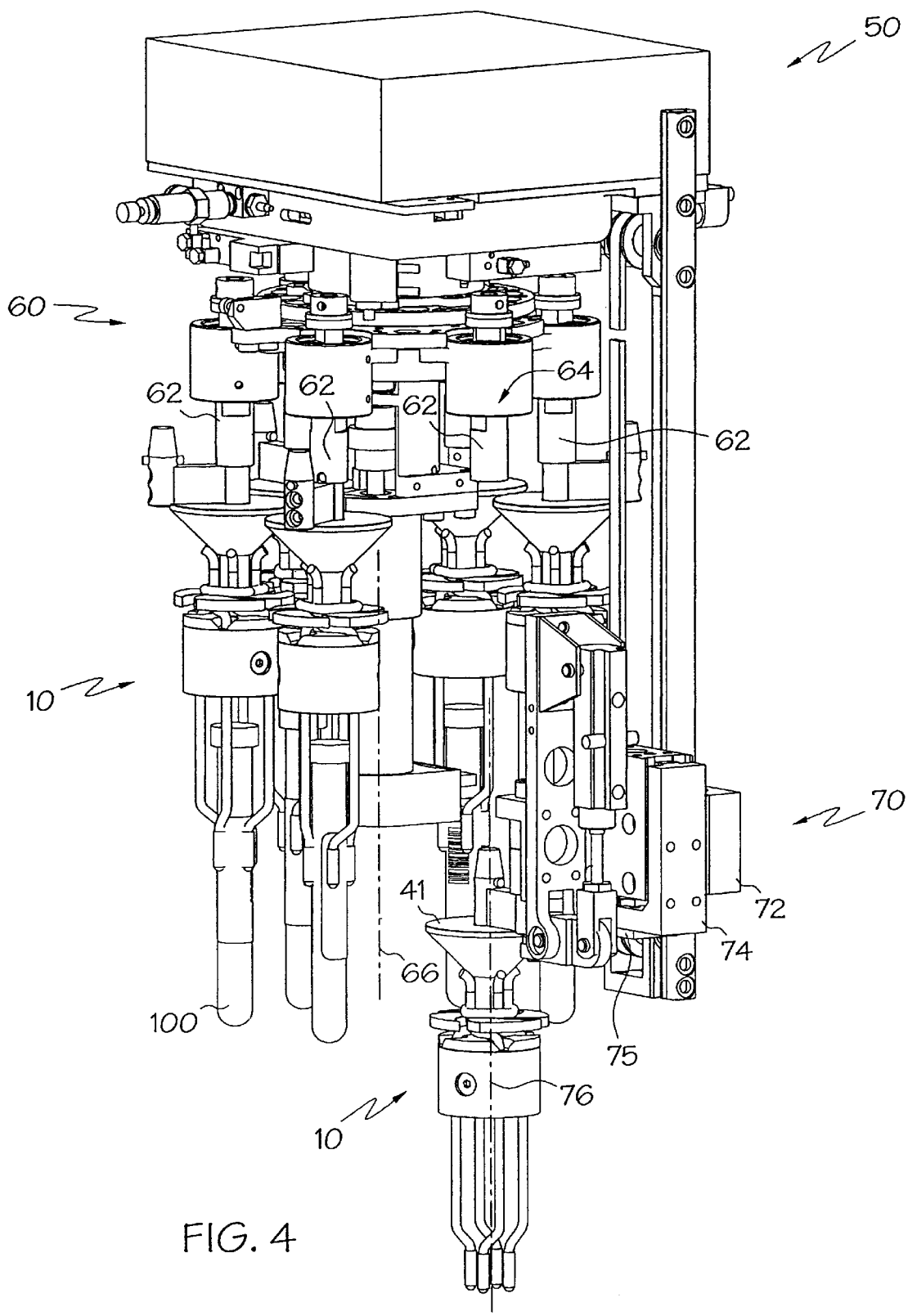
Figure 5:
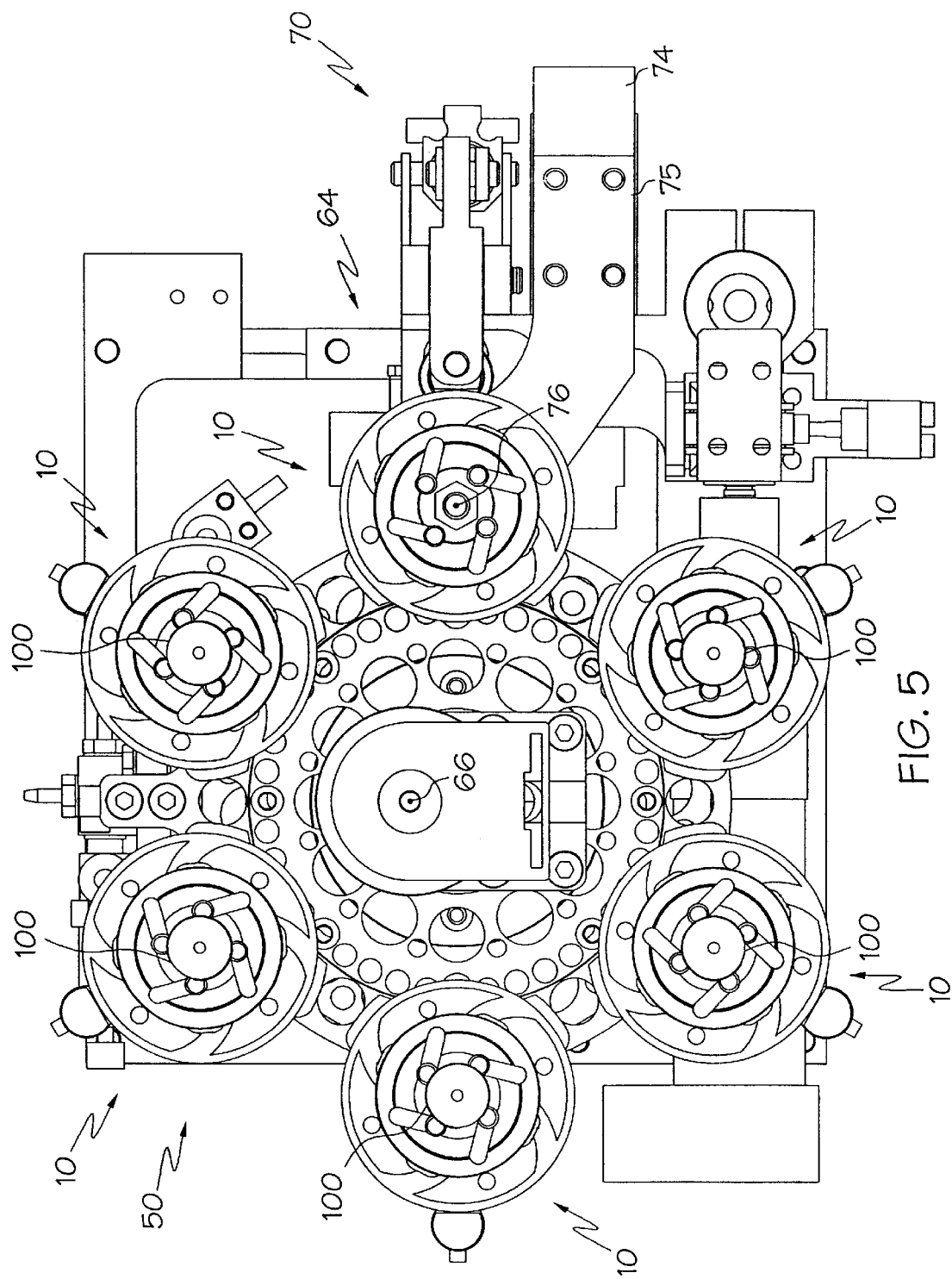
FIG. 5 is a bottom view of an object manipulator according to the present invention.

Referring now to FIGS. 3–5, an object manipulator 50 according to the present invention includes a rotary turret assembly 60 and a plurality of gripper assemblies 10. The rotary turret assembly 60 defines a plurality of gripper assembly stations 62. One of the gripper assembly stations is positioned in a gripper pick/place position 64. Individual gripper assemblies 10 are arranged in respective ones of the gripper assembly stations 62. The rotary turret assembly 60 is arranged to rotate the gripper assembly stations 62 about a turret axis 66 so as to position a selected one of the gripper assembly stations 62 in the pick/place position 64.

The rotary turret assembly 60 includes a gripper actuator assembly 70 arranged to cause a gripper assembly 10 positioned in the pick/place position 64 to execute an object pick/place operation. In the illustrated embodiment, each gripper assembly 10 is is removably secured in respective ones of the gripper assembly stations 62. For example, a magnetic coupling 12 (see FIGS. 1A, 1B, 2A, and 2B) may be provided to removably secure each gripper assembly 10 in respective ones of the gripper assembly stations 62.

The gripper actuator assembly 70 is arranged to remove a gripper assembly 10 positioned in the pick/place position 64 from one of the gripper assembly stations 62. The gripper actuator assembly 70 is further arranged to actuate the finger spreader 40 of the gripper assembly 10 positioned in the pick/place position 64. Typically, the actuation of the finger spreader 40 is executed following removal of the gripper assembly 10 from the gripper assembly station 62 but it may be executed prior to removal as well.

The gripper actuator assembly 70 is provided with a Z-axis drive 72 arranged to move a selected gripper assembly 10 along a Z-axis 76 parallel to the turret axis 66 to enable removal of the gripper assembly 10 positioned in the pick/place position 64 from the gripper assembly station 62. The gripper actuator assembly 70 is further provided with a spreader actuator 74 arranged to engage a selected finger spreader 40 and move the finger spreader 40 in the direction A along an axis parallel to the turret axis 66. In the illustrated embodiment, the spreader actuator 74 includes a paddle 75 that is arranged to engage the flat top surface 41 of the finger spreader 40.

For the purposes of describing and defining the present invention, it is noted that an object pick/place operation comprises an operation whereby an object is either transferred from an object holder to the manipulator 50 (picked) or transferred from the manipulator 50 to the object holder (placed). An object pick/place operation according to one embodiment of the present invention is illustrated in FIGS. 6–9. However, it is contemplated that the present invention is not limited to the specific pick/place operation described in FIGS. 6–9.

Referring now to FIGS. 6–9, an object manipulation system and a pick/place operation according to one embodiment of the present invention are described in detail. The object manipulation system comprises an X-Y positioner 80 arranged to move It within an X-Y plane 82. The X-Y plane 82 is displaced from and parallel to an object plane 102 defined by a plurality of test tubes or other objects 100. The object manipulator 50 is coupled to the X-Y positioner 80 so as to be movable with the X-Y positioner 80. It is noted that although FIGS. 6–9 primarily illustrate a pick operation, the steps associated with a place operation may be readily discerned therefrom.

Initially, the X-Y positioner 80 is activated to move the object manipulator 50 such that the gripper pick/place position 64 corresponds to the location of the object 100 to be picked. At the beginning of the pick cycle, the rotary turret assembly 60 indexes an empty gripper assembly 10 into the gripper pick/place position 64 (see FIG. 6). At this point, the gripper actuator assembly 70 has not yet engaged the gripper assembly 10 in the gripper pick/place position 64. More specifically, the Z-axis drive 72 holds the actuator assembly 70 at the upper end of the Z-axis 76.

Figure 7:
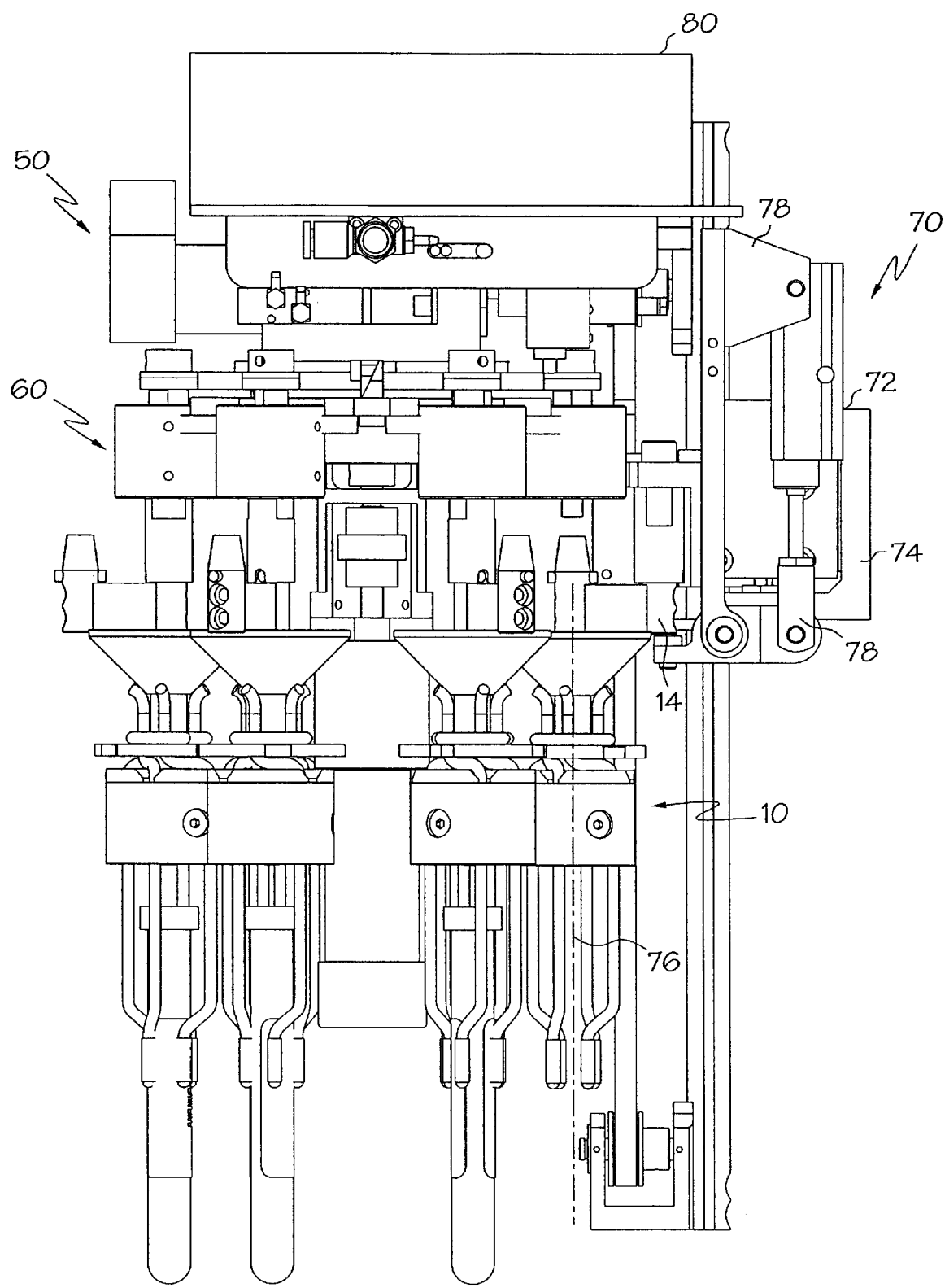

Next, the Z-axis drive 72 moves the actuator assembly 70 along the Z-axis 76 to allow the actuator assembly 70 to engage the tapered arm 14 of the gripper assembly 10 (see FIGS. 6 and 7). The actuator assembly 70 includes a lock mechanism 78 arranged to close about the gripper assembly 10 in the manner illustrated in FIG. 7.

Figure 8:
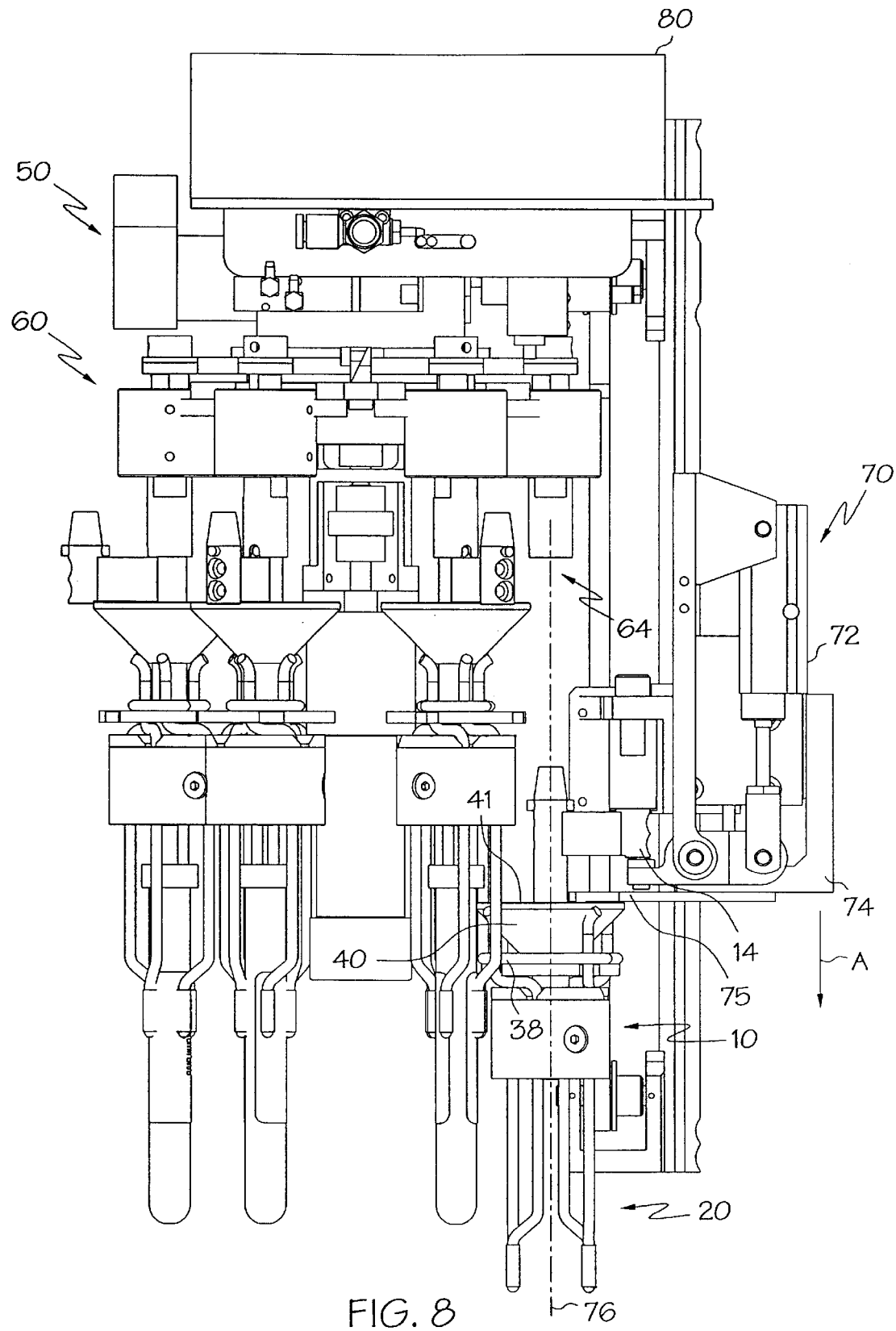

Once the gripper assembly 10 is securely engaged by the actuator assembly 70, the Z-axis drive 72 moves the actuator assembly 70 further along the Z-axis so as to remove the gripper assembly 10 positioned in the pick/place position 64 from the gripper assembly station 62 (see FIG. 8). In the illustrated embodiment, the Z-axis drive 72 need merely be powerful enough to overcome the force of the magnetic coupling 12 described above with reference to FIGS. 1A, 1B, 2A, and 2B.

As is noted above, the gripper actuator assembly 70 is further provided with a spreader actuator 74 arranged to engage a selected finger spreader 40 and move the finger spreader 40 in the direction A along an axis parallel to the Z-axis 76 so as to open the gripper fingers 20. In the illustrated embodiment, the spreader actuator 74 includes a paddle 75 that is arranged to engage the flat top surface 41 of the finger spreader 40 (see FIG. 8). Typically, the spreader actuator 74 is engaged following removal of the gripper assembly 10 from the gripper assembly station 62. The gripper fingers 20 are illustrated in the open position in FIG. 8.

Figure 9:
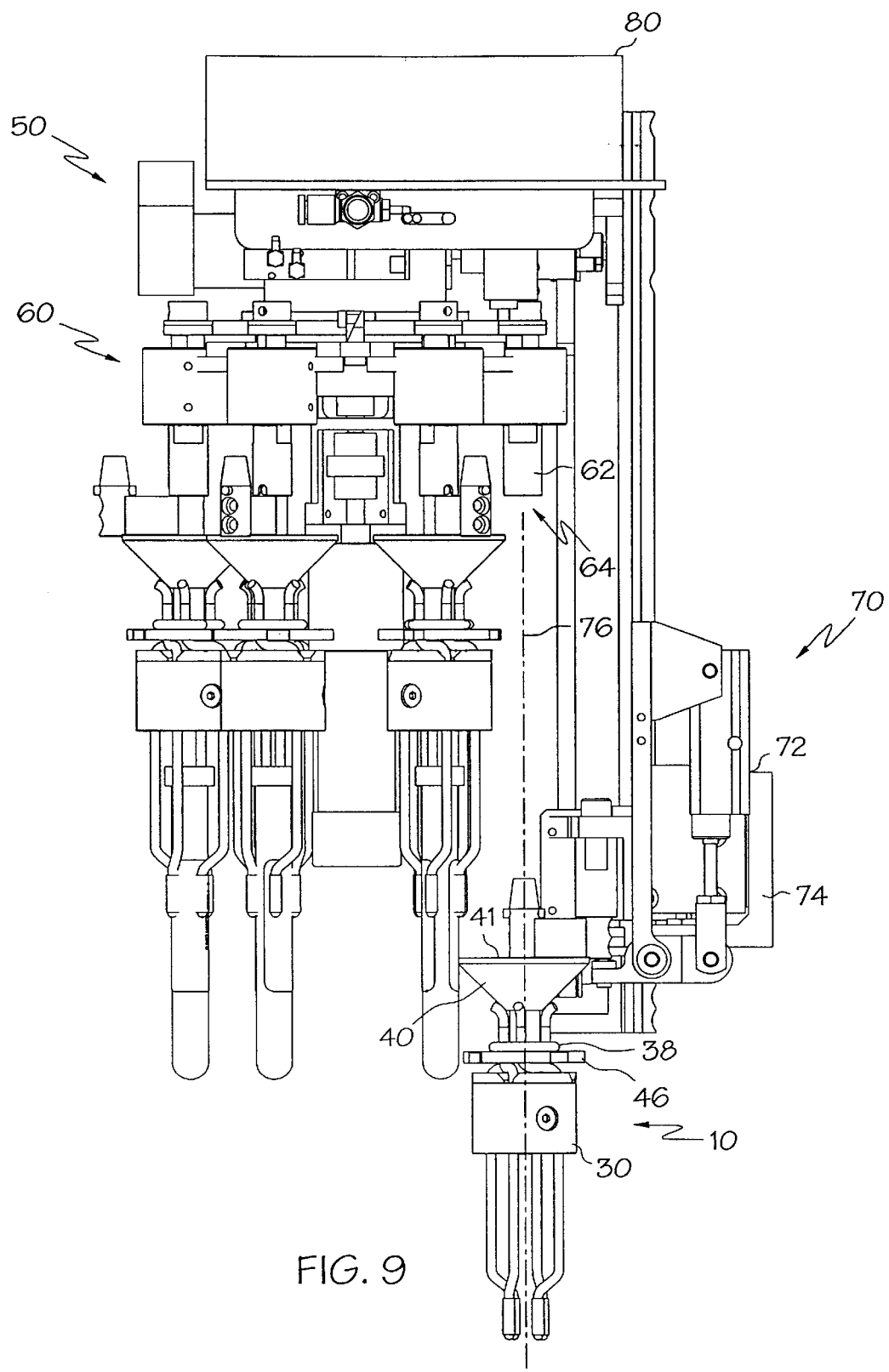

At the bottom of the Z-axis stroke, the gripper actuator assembly 70 allows the finger spreader 40 to return to the finger closed position under the biasing force of the biasing member 38 and grip a selected object 100 (see FIGS. 6 and 9, object 100 shown in FIG. 6). The Z-axis drive 72 is then activated to return the object 100 and the gripper assembly 10 to the gripper assembly station 62 in the gripper pick/place position 64. The rotary turret assembly 60 indexes the next empty gripper assembly 10 to the gripper pick/place position 64 to prepare for another pick operation.

It is noted that standard materials, e.g., stainless steel, tool steel, aluminum. etc., may be used to construct the various structural components of the present invention.

According to one embodiment of the present invention, the gripper finger bracket 46, the gripper finger pivot assembly 30, and the finger spreader 40 are constructed of Delrin® acetal resin, a crystalline plastic made by the polymerization of formaldehyde, available from DuPont. The gripper fingers 20 are constructed of stainless steel wire.

Figure 10:
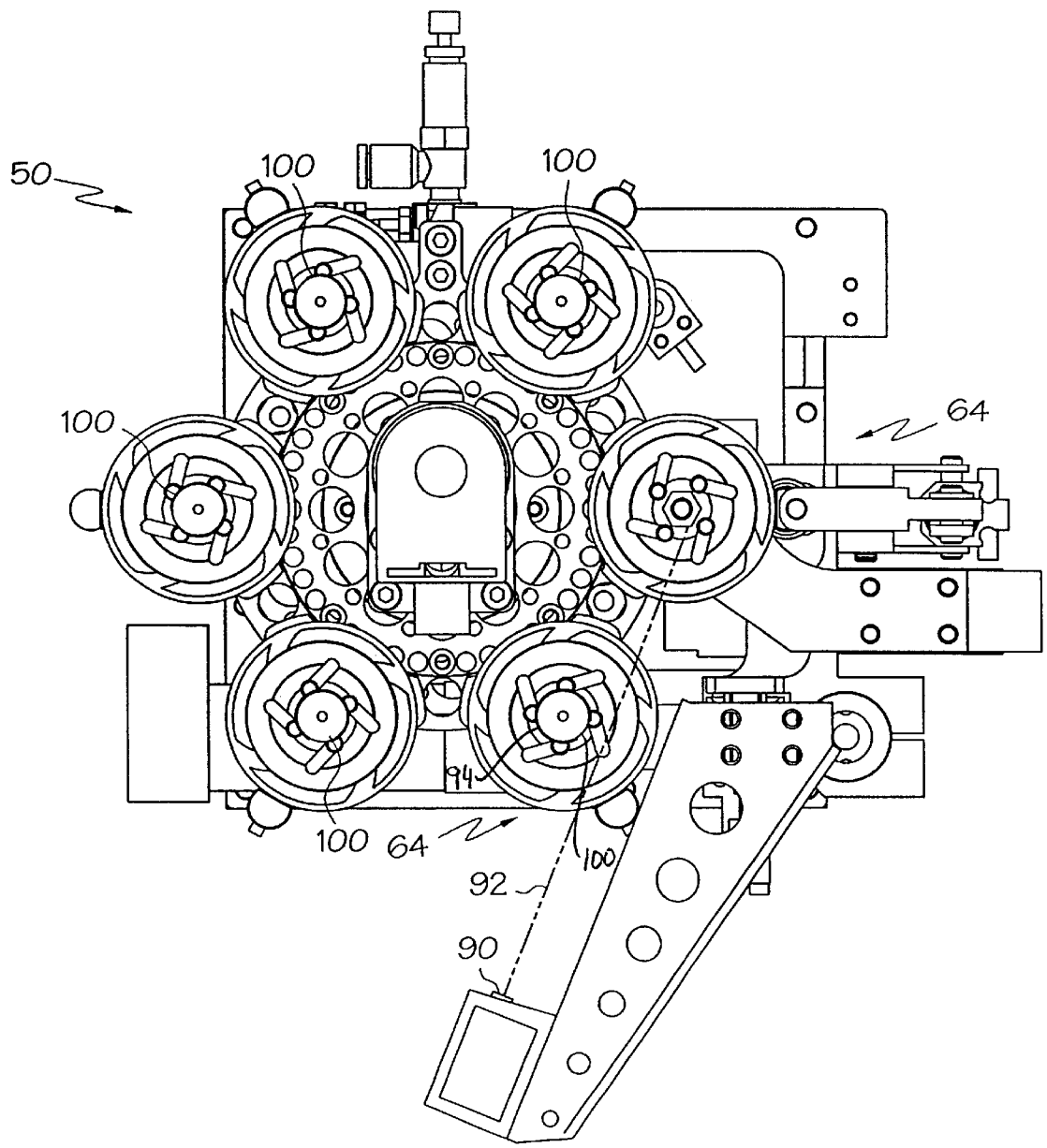
FIG. 10 illustrates an object manipulator according to the present invention incorporating a bar code reader.

Referring now to FIG. 10, an additional embodiment of the present invention is illustrated. In the FIG. 10 embodiment, a bar code reader assembly 90 is secured to the object manipulator 50 and is positioned to read a bar code label 94 present on an abject 100 held by the gripper assembly 10 moving from the pick/place position 64 to the next indexed position 64'. The object manipulator 50 and rotary turret assembly 60 may be arranged to cause the gripper assembly 10 to rotate 360° as it indexes from the pick/place position 64 to the next indexed position 64'. In this manner, the bar code present on the object 100 is assured to be moved through the field of view of the reader 90 along the reader beam projection 92 as it indexes from the pick/place position 64 to the next indexed position 64', regardless of the orientation of the object 100 in the gripper assembly 10.

The gripper fingers 20 of the present invention are particularly well-suited for the embodiment of the present invention illustrated in FIG. 10 because their dimensions and arrangement are such that they avoid substantial interference with the field of view of the reader 90. It is contemplated by the present invention that the reader 90 may comprise a conventional bar code reader or any other type of electromagnetic device for reading identification indicia present on the object 100. The bar code information may be utilized to identify the object 100 that has been picked and make decisions as to where to locate the object 100.

Having described the invention in detail and by reference to preferred embodiments thereof, it will be apparent that modifications and variations are possible without departing from the scope of the invention defined in the appended claims.

What is claimed is:

1. An object manipulator including a gripper assembly arranged to grip and release an object, wherein said gripper assembly comprises:
   a plurality of gripper fingers, each of said gripper fingers including
      a camming surface portion,
      a bearing surface portion, and
      an object engaging portion;
   a gripper finger pivot assembly arranged to accommodate respective bearing surface portions of said plurality of gripper fingers and wherein said gripper finger pivot assembly is arranged to define respective passages there through, and wherein said respective passages are arranged to accommodate respective bearing surface portions of said plurality of gripper fingers, and wherein each gripper finger has a pivot axis that is parallel to the longitudinal axis of that particular gripper finger; and
   a finger spreader positioned to progressively engage respective camming surface portions of said plurality of gripper fingers, wherein said gripper fingers are shaped and said pivot assembly is arranged such that progressive engagement of respective camming surface portions by said finger spreader causes said object engaging portions to be drawn away from each other and such that progressive disengagement of respective camming surface portions and said finger spreader causes said object engaging portions to be drawn towards each other.

2. An object manipulator as claimed in claim 1 wherein said camming surface portion, said bearing surface portion, and said object engaging portion are arranged in succession along each of said gripper fingers.

3. An object manipulator as claimed in claim 1 wherein, upon disengagement of respective camming surface portions and said finger spreader, said object engaging portions converge radially inwards relative to said bearing surface portions.

4. An object manipulator as claimed in claim 1 wherein said bearing surface portion is substantially straight.

5. An object manipulator as claimed in claim 1 wherein said gripper finger pivot assembly is arranged to define respective passages there through, and wherein said respective passages are arranged to accommodate respective bearing surface portions of said plurality of gripper fingers.

6. An object manipulator as claimed in claim 5 wherein:
   said bearing surface portions of said plurality of gripper fingers define a circular finger cross section; and said respective passages define a circular passage cross section slightly larger than said circular finger cross section.

7. An object manipulator as claimed in claim 6 wherein said gripper finger fit comprise a radial portion arranged to define a path of movement of said object engaging portion upon said progressive engagement of said respective camming surface portions.

8. An object manipulator as claimed in claim 1 further comprising a biasing member arranged to urge said object engaging portions towards each other.

9. An object manipulator as claimed in claim 8 wherein said biasing member comprises a constrictive band arranged about said gripper fingers.

10. An object manipulator as claimed in claim 1 further comprising a biasing member arranged to oppose progressive engagement of respective camming surface portions by said finger spreader.

11. An object manipulator as claimed in claim 1 wherein said plurality of gripper fingers are shaped such that, upon progressive engagement of said camming surface portions by said finger spreader, a path of movement of said object engaging portions follows a path of movement of said camming surface portions.

12. An object manipulator as claimed in claim 1 wherein said finger spreader is arranged to initially engage said camming surface portions at a first cross sectional portion thereof and subsequently engage said camming surface at progressively larger cross sectional portions thereof.

13. An object manipulator as claimed in claim 12 wherein said first cross sectional portion and said progressively larger cross sectional portions of said finger spreader are circular.

14. An object manipulator as claimed in claim 1 further comprising an axial stop against which said causing surface portions are arranged to rest upon disengagement of said canning surface portions and said finger spreader.

15. An object manipulator as claimed in claim 14 wherein said axial stop defines an axial stop cross section that is no larger than a cross section of an object to be manipulated.

16. An object manipulator as claimed in claim 14 wherein said axial stop defines a circular axial stop cross section.

17. An object manipulator as claimed in claim 14 wherein said finger spreader is arranged to progressively engage and disengage said camming surface portions by moving along said axial stop.

18. An object manipulator as claimed in claim 1 further comprising a gripper finger bracket arranged along said gripper fingers between respective camming surface portions and respective bearing surface portions, wherein said gripper finger bracket is arranged to define respective finger bracket apertures through which respective gripper fingers move upon progressive engagement and disengagement of said camming surface portions by sad finger spreader.

19. An object manipulator as claimed in claim 18 wherein said respective finger bracket apertures define an arcuate shape.

20. An object manipulator as claimed in claim 1 further comprising:
   a gripper finger bracket arranged along sad gripper fingers between respective camming surface portions and respective bearing surface portions, wherein said gripper finger bracket is arranged to define respective finger bracket apertures through which respective gripper fingers move upon progressive engagement and disengagement of said camming surface potions by said finger spreader, and
   a biasing member arranged to urge said object engaging portions towards each other, wherein said biasing member comprises a constrictive band arranged about said gripper fingers adjacent said gripper finger bracket.

21. An object manipulator comprising:
   a rotary turret assembly defining a plurality of gripper assembly stations and a gripper pick/place position, wherein said rotary turret assembly is arranged to rotate sad gripper assembly stations about a turret axis so as to position a selected one of said gripper assembly stations in said pick/place position; and
   a plurality of gripper assemblies arranged in respective ones of said gripper assembly stations, wherein said rotary turret assembly includes a gripper actuator assembly arranged to cause a gripper assembly positioned in said pick/place position to execute an object pick/place operation, wherein said plurality of gripper assemblies are removably secured in respective ones of said gripper assembly stations, and wherein said gripper actuator is arranged to remove a gripper assembly positioned in said pick/place position from one of said gripper assembly stations.

22. An object manipulator as claimed in claim 21 wherein said plurality of gripper assemblies are removably secured in respective ones of said gripper assembly stations through magnetic coupling of said gripper assemblies and said gripper assembly stations.

23. An object manipulator as claimed in claim 21 wherein:
   each of said gripper assemblies comprise
      a plurality of gripper fingers and
      a finger spreader positioned to progressively engage respective camming surface portions of said plurality of gripper fingers, wherein said gripper assembly is arranged such that progressive engagement of respective camming surface portions of said gripper fingers by said finger spreader causes object engaging portions of said gripper fingers to be drawn away from each other and such that progressive disengagement of respective camming surface portions of said gripper fingers and said finger spreader causes said object engaging portions to be drawn towards each other; and
   said gripper actuator is further arranged to actuate a finger spreader of a gripper assembly positioned in said pick/place position following removal of said gripper assembly from one of said gripper assembly stations.

24. An object manipulator as claimed in claim 23 wherein said gripper actuator assembly further comprises a spreader actuator arranged to engage a selected finger spreader and move said selected finger spreader along an axis parallel to said turret axis.

25. An object manipulator as claimed in claim 21 wherein said gripper actuator assembly further comprises a Z-axis drive arranged to move a selected gripper assembly along a Z-axis parallel to said turret axis.

26. An object manipulator as claimed in claim 21 wherein each of said gripper assemblies comprise:
   a plurality of gripper fingers, each of said gripper fingers including
      a camming surface portion,
      a bearing surface portion, and
      an object engaging portion; a gripper finger pivot assembly arranged to accommodate respective bearing surface portions of said plurality of gripper fingers; and
   a finger spreader positioned to progressively engage respective camming surface portions of said plurality of gripper fingers, wherein said gripper fingers are shaped and said pivot assembly is arranged such that progressive engagement of respective camming surface potions by said finger spreader causes said object engaging portions to be drawn away from each other and such that progressive disengagement of respective camming surface portions and said finger spreader causes said object engaging portions to be drawn towards each other.

27. An object manipulator as claimed in claim 26 wherein, upon disengagement of respective camming surface portions and said finger spreader, said object engaging portions converge radially inwards relative to said bearing surface portions.

28. An object manipulator as claimed in claim 26 further comprising a bar code reader secured to said object manipulator.

29. An object manipulator as claimed in claim 28 wherein said bar code reader defines a field of view encompassing said pick/place position.

30. An object manipulation system comprising:
- a plurality of objects arranged in an object plane;
- an X-Y positioner arranged to move within an X-Y plane, wherein said X-Y plane is displaced from and parallel to said object plane; and
- an object manipulator coupled to said X-Y positioner so as to be movable with said X-Y positioner, wherein said object manipulator comprises
    - a rotary turret assembly defining a plurality of gripper assembly stations and a gripper pick/place position, wherein said rotary turret assembly is arranged to rotate said gripper assembly stations about a turret axis so as to position a selected one of said gripper assembly stations in said pick/place position, and
    - a plurality of gripper assemblies arranged in respective ones of said gripper assembly stations, wherein said rotary turret assembly includes a gripper actuator assembly arranged to cause a gripper assembly positioned in said pick/place position to execute an object pick/place operation on one of said objects in said object plane.

31. An object manipulation system as claimed in claim 30 wherein each of said gripper assemblies comprise:
- a plurality of gripper fingers, each of said gripper fingers including
    - a camming surface portion,
    - a bearing surface portion, and
    - an object engaging portion;
- a gripper finger pivot assembly arranged to accommodate respective bearing surface portions of said plurality of gripper fingers; and
- a finger spreader positioned to progressively engage respective camming surface portions of said plurality of gripper fingers, wherein said gripper fingers are shaped and said pivot assembly is arranged such that progressive engagement of respective camming surface portions by said finger spreader causes said object engaging portions to be drawn away from each other and such tat progressive disengagement of respective camming surface portions and said finger spreader causes said object engaging portions to be drawn towards each other.

32. An object manipulator as claimed in claim 31 wherein, upon disengagement of respective camming surface portions and said finger spreader, said object engaging portions converge radially inwards relative to said bearing surface portions.

33. An object manipulator as claimed in claim 30 further comprising a bar code reader secured to said object manipulator.

34. An object manipulator as claimed in claim 30 wherein said bar code reader defines a field of view encompassing said pick/place position.

35. An object manipulation system as claimed in claim 30 further comprising:
- at least one additional X-Y positioner arranged to move parallel to said object plane;
- an additional object manipulator coupled to each of said additional X-Y positioners so as to be movable with said X-Y positioner.

36. An object manipulator including a gripper assembly arranged to grip and release an object, wherein said gripper assembly comprises:
- a plurality of gripper fingers, each of said gripper fingers including
    - a camming surface portion,
    - a bearing surface portion, wherein said bearing surface portions of said plurality of gripper fingers define a circular finger cross section; and
    - an object engaging portion;
- a gripper finger pivot assembly arranged to accommodate respective bearing surface portions of said plurality of gripper fingers and wherein said gripper finger pivot assembly is arranged to define respective passages there through, and wherein said respective passages are arranged to accommodate respective bearing surface portions of said plurality of gripper fingers, and wherein the pivot axis of each gripper finger is located in a position that is parallel to said bearing surface portion of said finger; and
- a finger spreader positioned to progressively engage respective camming surface portions of said plurality of gripper fingers, wherein said gripper fingers are shaped and said pivot assembly is arranged such that progressive engagement of respective camming surface portions by said finger spreader causes said object engaging portions to be drawn away from each other and such that progressive disengagement of respective camming surface portions and said finger spreader causes said object engaging portions to be drawn towards each other.

* * * * *

UNITED STATES PATENT AND TRADEMARK OFFICE
CERTIFICATE OF CORRECTION

PATENT NO.   : 6,435,582 B1
DATED        : August 20, 2002
INVENTOR(S)  : DaSilva et al.

It is certified that error appears in the above-identified patent and that said Letters Patent is hereby corrected as shown below:

Column 8,
Line 54, "gripper finger fit comprise" should be -- gripper fingers further comprise --;

Column 9,
Line 17, "said causing surface" should be -- said camming surface --;
Line 19, "said canning surface" should be -- said camming surface --;
Line 58, "rotate sad gripper" should be -- rotate said gripper --;

Column 11,
Line 40, "such tat progressive" should be -- such that progressive --.

Signed and Sealed this

Eighteenth Day of February, 2003

JAMES E. ROGAN
*Director of the United States Patent and Trademark Office*